United States Patent
Podhorez et al.

(10) Patent No.: US 7,868,027 B2
(45) Date of Patent: Jan. 11, 2011

(54) PROCESS FOR THE PREPARATION OF CERTAIN SUBSTITUTED SULFILIMINES

(75) Inventors: David E. Podhorez, Midland, MI (US); Ronald Ross, Jr., Zionsville, IN (US); James R. McConnell, Midland, MI (US)

(73) Assignee: Dow AgroSciences LLC, Indianapolis, IN (US)

( * ) Notice: Subject to any disclaimer, the term of this patent is extended or adjusted under 35 U.S.C. 154(b) by 505 days.

(21) Appl. No.: 12/069,627

(22) Filed: Feb. 12, 2008

(65) Prior Publication Data

US 2008/0207910 A1     Aug. 28, 2008

Related U.S. Application Data

(60) Provisional application No. 60/903,471, filed on Feb. 26, 2007.

(51) Int. Cl.
*A61K 31/44* (2006.01)
(52) U.S. Cl. ...................................... 514/357
(58) Field of Classification Search .................. 514/357
See application file for complete search history.

(56) References Cited

U.S. PATENT DOCUMENTS

2005/0228027 A1    10/2005    Zhu

OTHER PUBLICATIONS

U.S. Appl. No. 11/704,756, filed Feb. 9, 2007, Kim E. Arndt.
*Penicillin N-Cyanosulphilimines; Cyanamide/Iodobenze, Diacetate . . .* ; Tetrahedron Letters No. 39, Pergamon Press Ltd. 1979, pp. 3781-3784.
*Sulfilimines and Related Derivative*, by Oae, Shigeru and Furukawa, Naomichi; ACS Monograph 179, American Chemical Society, 1983.
PCT/US2008/001818, International Search Report, Jul. 23, 2008, Dow AgroSciences LLC [David E. Podhorez et al.].
PCT/US2008/001818, Written Opinion of the ISA, Jul. 23, 2008, Dow AgroSciences LLC [David E. Podhorez et al.].

*Primary Examiner*—Rita J Desai
*Assistant Examiner*—John Mabry
(74) *Attorney, Agent, or Firm*—Carl D. Corvin; Craig E. Mixan

(57) ABSTRACT

Cyano-substituted sulfilimines are produced efficiently and in high yield from the corresponding sulfides by reaction with cyanamide and hypochlorite.

7 Claims, No Drawings

US 7,868,027 B2

PROCESS FOR THE PREPARATION OF CERTAIN SUBSTITUTED SULFILIMINES

CROSS REFERENCE TO RELATED APPLICATION

This non-provisional application claims priority from provisional application 60/903,471 filed Feb. 26, 2007, and hereby incorporates the entire disclosure thereof herein.

BACKGROUND OF THE INVENTION

The present invention concerns a process for preparing certain substituted sulfilimines.

The substituted sulfilimines are useful intermediates for the preparation of certain new insecticidal sulfoximines; see, for example, U.S. Patent Publication 2005/0228027 in which cyano-substituted sulfilimines are prepared by the reaction of the corresponding sulfide with cyanamide in the presence of iodobenzene diacetate. It would be advantageous to produce the sulfilimines efficiently and in high yield from the corresponding sulfides without having to use iodobenzene diacetate, which, in addition to its expense, presents waste disposal problems.

SUMMARY OF THE INVENTION

In the present invention, iodobenzene diacetate is replaced by hypochlorite. In addition to being low cost, hypochlorite eliminates the severe waste issues associated with iodobenzene diacetate. Thus, the present invention concerns a process for preparing certain substituted sulfilimines, having the general structure of (I),

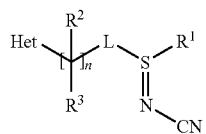

wherein

Het represents:

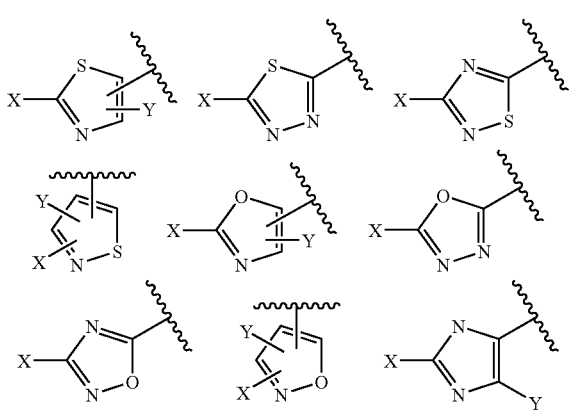

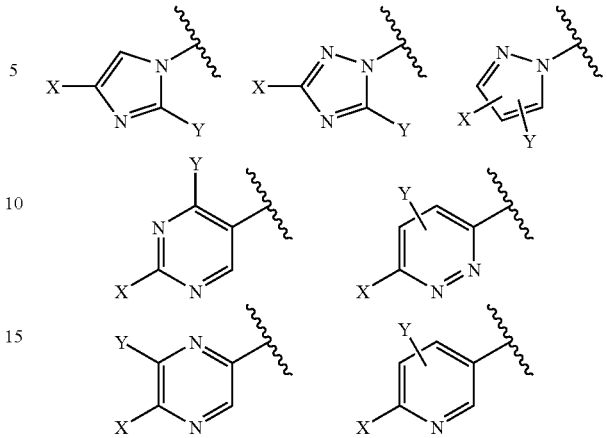

X represents halogen, $C_1$-$C_4$ alkyl, $C_1$-$C_4$ haloalkyl, $C_2$-$C_4$ alkenyl, $C_2$-$C_4$ alkynyl, $C_2$-$C_4$ haloalkenyl, $C_1$-$C_4$ alkoxy, $C_1$-$C_4$ haloalkoxy, CN, $NO_2$, $SO_mR^6$ where m is an integer from 0-2, $COOR^4$ or $CONR^4R^5$;

Y represents hydrogen, halogen, $C_1$-$C_4$ alkyl, $C_1$-$C_4$ haloalkyl, $C_2$-$C_4$ alkenyl, $C_2$-$C_4$ alkynyl, $C_2$-$C_4$ haloalkenyl, $C_1$-$C_4$ alkoxy, $C_1$-$C_4$ haloalkoxy, CN, $NO_2$, $SO_mR^1$ where m is an integer from 0-2, $COOR^4$, $CONR^4R^5$, aryl or heteroaryl;

n is an integer from 0-3;

L represents either a single bond, —$CH(CH_2)_p$— where $R^1$, S and L taken together represent a 4-, 5-, or 6-membered ring and p is an integer from 1-3, —CH($CH_2OCH_2$)— where $R^1$, S and L taken together represent a 6-membered ring, or —CH— where L, $R^2$ and the common carbon to which they connect taken together represent a 4-, 5-, or 6-membered ring with up to, but no more than, 1 heteroatom;

$R^1$ represents $C_1$-$C_4$ alkyl, $C_1$-$C_4$ haloalkyl, $C_3$-$C_6$ alkenyl, $C_3$-$C_6$ alkynyl, $C_3$-$C_6$ haloalkenyl, arylalkyl, heteroarylalkyl, or —$CH_2$— in cases where $R^1$, S and L taken together represent a 4-, 5-, or 6-membered ring;

$R^2$ and $R^3$ independently represent hydrogen, halogen, $C_1$-$C_4$ alkyl, $C_1$-$C_4$ haloalkyl, $C_2$-$C_4$ alkenyl, $C_2$-$C_4$ alkynyl, $C_2$-$C_4$ haloalkenyl, $C_1$-$C_4$ alkoxy, $C_1$-$C_4$ haloalkoxy, CN, $SO_mR^6$ where m is an integer from 0-2, $COOR^4$, $CONR^4R^5$, arylalkyl, heteroarylalkyl, or $R^2$ and $R^3$ and the common carbon to which they attach form a 3-6 membered ring;

$R^4$ and $R^5$ independently represent hydrogen, $C_1$-$C_4$ alkyl, $C_1$-$C_4$ haloalkyl; $C_3$-$C_6$ alkenyl, $C_3$-$C_6$ alkynyl, $C_3$-$C_6$ haloalkenyl, aryl, heteroaryl, arylalkyl or heteroarylalkyl; and $R^6$ represents $C_1$-$C_4$ alkyl, $C_1$-$C_4$ haloalkyl, $C_3$-$C_6$ alkenyl, $C_3$-$C_6$ alkynyl, $C_3$-$C_6$ haloalkenyl, arylalkyl or heteroarylalkyl;

which comprises contacting a sulfide of formula (II)

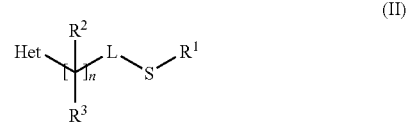

wherein

R[1], R[2], R[3], L, Het and n are as previously defined with cyanamide and hypochlorite solution at a temperature from about −40° C. to about 30° C. in a suitable organic solvent that is essentially inert to the reaction conditions.

The process is well suited to prepare sulfilimines of the following classes:

(1) Compounds of formula (I) wherein Het is (6-substituted)pyridin-3-yl and where X is halogen or $C_1$-$C_2$ haloalkyl and Y is hydrogen.

(2) Compounds of formula (I) wherein R[2] and R[3] are as previously defined, R[1] is methyl, n is 1, and L is a single bond, having the structure:

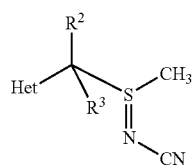

(3) Compounds of formula (I) wherein n is 1, R[1], S and L taken together form a standard 4-, 5-, or 6-membered ring such that L is —CH(CH$_2$)$_p$— and p is an integer from 1-3, and R[1] is —CH$_2$— having the structure:

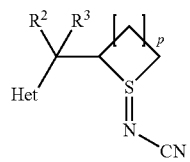

(4) Compounds of formula (I) wherein n is 0, R[1], S and L taken together form a standard 4-, 5-, or 6-membered ring such that L is —CH(CH$_2$)$_p$— and p is an integer from 1-3, and R[1] is —CH$_2$— having the structure:

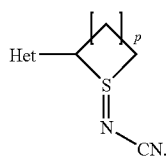

DETAILED DESCRIPTION OF THE INVENTION

Throughout this document, all temperatures are given in degrees Celsius, and all percentages are weight percentages unless otherwise stated.

The terms "alkyl", "alkenyl" and "alkynyl", as well as derivative terms such as "alkoxy", "acyl", "alkylthio", "arylalkyl", "heteroarylalkyl" and "alkylsulfonyl", as used herein, include within their scope straight chain, branched chain and cyclic moieties. Thus, typical alkyl groups are methyl, ethyl, 1-methylethyl, propyl, 1,1-dimethylethyl, and cyclopropyl. Unless specifically stated otherwise, each may be unsubstituted or substituted with one or more substituents selected from but not limited to halogen, hydroxy, alkoxy, alkylthio, $C_1$-$C_6$ acyl, formyl, cyano, aryloxy or aryl, provided that the substituents are sterically compatible and the rules of chemical bonding and strain energy are satisfied. The term "haloalkyl" and "haloalkenyl" includes alkyl and alkenyl groups substituted with from one to the maximum possible number of halogen atoms, all combinations of halogens included. The term "halogen" or "halo" includes fluorine, chlorine, bromine and iodine, with fluorine being preferred. The terms "alkenyl" and "alkynyl" are intended to include one or more unsaturated bonds.

The term "aryl" refers to a phenyl, indanyl or naphthyl group. The term "heteroaryl" refers to a 5- or 6-membered aromatic ring containing one or more heteroatoms, viz., N, O or S; these heteroaromatic rings may be fused to other aromatic systems. The aryl or heteroaryl substituents may be unsubstituted or substituted with one or more substituents selected from halogen, hydroxy, nitro, cyano, aryloxy, formyl, $C_1$-$C_6$ alkyl, $C_2$-$C_6$ alkenyl, $C_2$-$C_6$ alkynyl, $C_1$-$C_6$ alkoxy, halogenated $C_1$-$C_6$ alkyl, halogenated $C_1$-$C_6$ alkoxy, $C_1$-$C_6$ acyl, $C_1$-$C_6$ alkylthio, $C_1$-$C_6$ alkylsulfinyl, $C_1$-$C_6$ alkylsulfonyl, aryl, $C_1$-$C_6$ OC(O)alkyl, $C_1$-$C_6$ NHC(O)alkyl, C(O)OH, $C_1$-$C_6$C(O)Oalkyl, C(O)NH$_2$, $C_1$-$C_6$C(O)NHalkyl, or $C_1$-$C_6$C(O)N(alkyl)$_2$, provided that the substituents are sterically compatible and the rules of chemical bonding and strain energy are satisfied.

The sulfide starting materials of Formula II or a process for their preparation have been disclosed in U.S. Patent Publication 2005/0228027. The sulfides (II) can be prepared in different ways as illustrated in Schemes A, B, C, D, E, F and G.

In Scheme A, the sulfide of formula (A$_1$), wherein L is a single bond, n is 1, R[3]═H, and R[1], R[2] and Het are as previously defined can be prepared from halides of formula (D) by nucleophilic substitution with the sodium salt of an alkyl thiol.

Scheme A

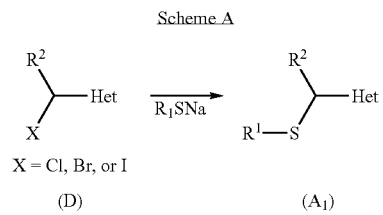

In Scheme B, the sulfide of formula (A$_2$), wherein L is a single bond, n is 3, R[3]═H, and R[1], R[2] and Het are as previously defined, can be prepared from the chloride of formula (E) by reacting with a 2-mono substituted methyl malonate in the presence of base such as potassium tert-butoxide to provide 2,2-disubstituted malonate, hydrolysis under basic conditions to form a diacid, decarboxylation of the diacid by heating to give a monoacid, reduction of the monoacid with borane-tetrahyrofuran complex to provide an alcohol, tosylation of the alcohol with toluenesulfonyl chloride (tosyl chloride) in the presence of a base like pyridine to give a tosylate and replacement of the tosylate with the sodium salt of the desired thiol.

Scheme B

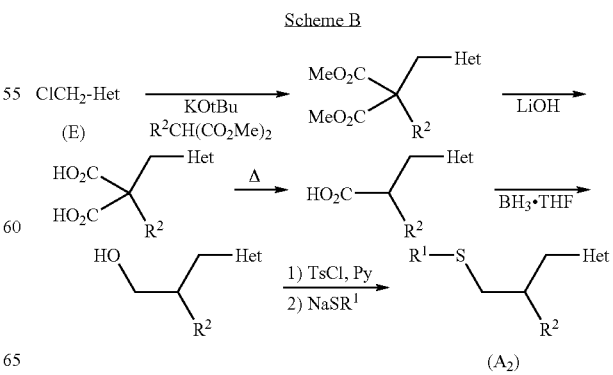

In Scheme C, the sulfide of formula (A₃), wherein L is a single bond, n is 2, R³═H, and R¹, R² and Het are as previously defined, can be prepared from the nitrile of formula (F) by deprotonation with a strong base and alkylation with an alkyl iodide to give α-alkylated nitrile, hydrolysis of the α-alkylated nitrile in the presence of a strong acid like HCl to give an acid, reduction of the acid with borane-tetrahyrofuran complex to provide an alcohol, tosylation of the alcohol with tosyl chloride in the presence of a base like pyridine to give a tosylate and replacement of the tosylate with the sodium salt of the desired thiol.

A more efficient protocol to access cyclic sulfides of formula (A₄) is illustrated in Scheme E where Het is a 6-substituted pyridin-3-yl and Z is previously defined. Accordingly, thiourea is added to a substituted chloromethyl pyridine, which, after hydrolysis, and alkylation with the appropriate bromo chloroalkane (p=1, 2, or 3) under aqueous base conditions, yields sulfide (H). Subsequent cyclization of (H) in the presence of a base like potassium-t-butoxide in a polar aprotic solvent such as THF provides cyclic sulfide (A₄).

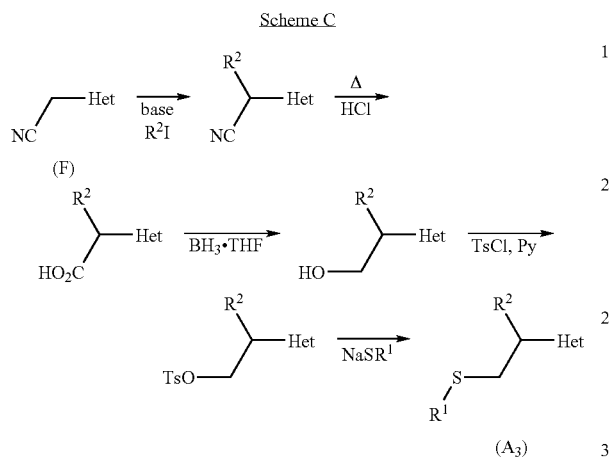

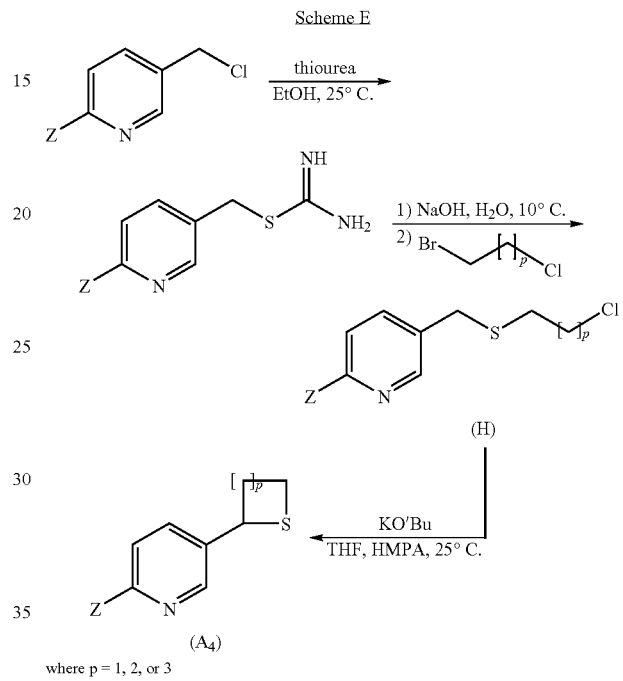

In Scheme D, the sulfide of formula (A₄), wherein n is 0, R¹ is —CH₂—, L is —CH(CH₂)$_p$— where p is either 2 or 3 and, taken together with R¹, S and L form a 5- or 6-membered ring, and Het is as previously described can be prepared from tetrahydrothiophene (p=2) or pentamethylene sulfide (p=3) (G). Chlorination of the cyclic sulfide starting material with N-chlorosuccinimide in benzene followed by alkylation with certain lithiated heterocycles or Grignard reagents can lead to the desired sulfides (A₄) in satisfactory yield.

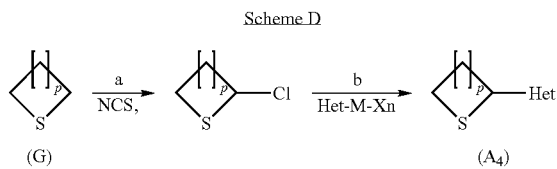

Certain sulfides of formula (A₁) wherein Het is a substituted pyridin-3-yl, Z is as previously defined, and R¹, R²═CH₃ can be prepared alternatively via methods illustrated in Scheme F. Accordingly, the appropriate enone is coupled with dimethylaminoacrylonitrile and cyclized with ammonium acetate in DMF to yield the corresponding 6-substituted nicotinonitrile. Treatment with methyl-magnesium bromide, reduction with sodium borohydride, chlorination with thionyl chloride, and nucleophilic substitution with the sodium salt of an alkyl thiol provides desired sulfides (A₁).

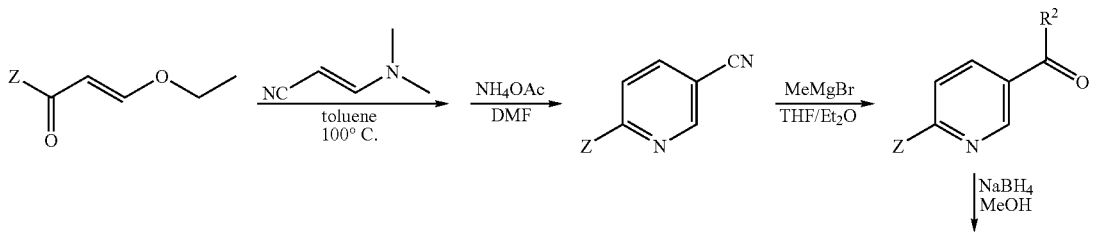

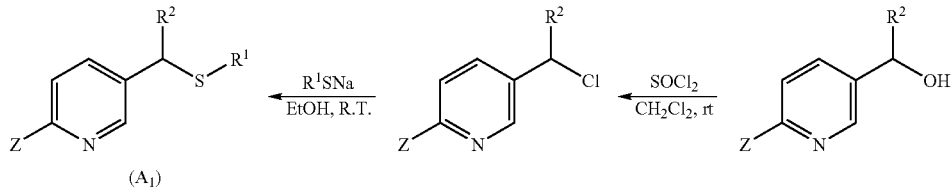

A variation of Scheme F is illustrated in Scheme G, wherein enamines, formed from the addition of an amine, e.g., pyrrolidine, with the Michael adduct of certain sulfides with appropriately substituted α,β-unsaturated aldehydes, are coupled with substituted enones and cyclized with ammonium acetate in $CH_3CN$ to yield the desired sulfides ($A_1$) wherein $R^1$, $R^2$, $R^3$, and Z are previously defined.

Scheme G

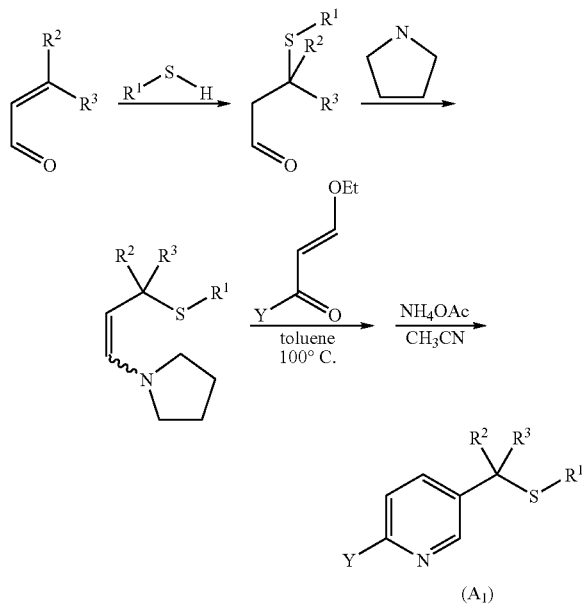

Cyanamide can be used as a solid or as an aqueous solution. The use of a 50 weight percent solution of cyanamide in water is often preferred. A stoichiometric amount of cyanamide is required, but it is often convenient to employ from about 0.9 to about 1.1 molar equivalents based on the amount of sulfide.

By hypochlorite solution is meant an aqueous solution of a metallic salt of hypochlorous acid. The metallic salt can be a Group I alkali metal salt or a Group II alkaline earth metal salt. The preferred hypochlorite salts are sodium hypochlorite or calcium hypochlorite. The aqueous hypochlorite solution usually contains from about 2 percent to about 12 percent hypochlorite salt, most preferably from about 5 percent to about 6 percent hypochlorite salt. It is often most convenient to use commercial Clorox™ bleach which contains about 5 to about 6 weight percent sodium hypochlorite in water. A stoichiometric amount of hypochlorite is required but it is often convenient to employ from about 0.95 to about 1.2 molar equivalents based on the amount of sulfide.

Salts of meta-bisulfite (such as sodium or potassium) can be used to quench any excess hypochlorite. The preferred salt of choice is sodium. The number of equivalents of metabisulfite can range from about 1.0 to about 5.0 relative to the hypochorite stoichiometry. The preferred range of equivalents is from about 2.0 to about 4.0 equivalents of metabisulfite per equivalent of hypochlorite remaining.

The process of the present invention is conducted in a suitable organic solvent that is essentially inert to the strong oxidizing conditions of the reaction. Particularly suitable organic solvents are aliphatic hydrocarbons like petroleum ether, aliphatic alcohols resistant to oxidation like t-butyl alcohol, halogenated aliphatic and halogenated aromatic hydrocarbons such as dichloromethane, chloroform, 1,2-dichloroethane and dichlorobenzene, and aliphatic and aromatic nitriles such as acetonitrile and benzonitrile. Halogenated aliphatic hydrocarbons and aliphatic nitriles are preferred. It is often convenient to perform the oxidation in a biphasic solvent system comprising a mixture of, for example, a halogenated aliphatic hydrocarbon such as dichloromethane and water. An organic solvent that can facilitate partitioning of the desired sulfilimine is also desirable, with acetonitrile being especially preferred.

The reaction temperature can range from about −40° C. to about 30° C. The preferred range is about −10° C. to about 10° C., with about −5° C. to about 0° C. being most preferred.

The reaction is conveniently carried out in a two step sequence. For example, hypochlorite can be added to a cold solution of cyanamide in an essentially inert solvent, followed by a second later addition of the sulfide. Alternatively, the cyanamide and sulfide can be mixed together in an essentially inert solvent, and the hypochlorite can added to this cold mixture directly. After addition of the hypochlorite, the reaction mixture is allowed to stir anywhere from 15 min to 2 hr, typically 30 min at 0° C. A small amount of aqueous metabisulfite solution is typically added to destroy excess oxidant, as determined via testing with starch-$I_2$ paper. At this point, the aqueous phase is separated from the organic sulfilimine phase. The organic solution of the sulfilimine can be used directly in a subsequent oxidation to an insecticidal sulfoximine or the sulfilimine can be isolated and purified by conventional techniques.

The following examples are presented to illustrate the invention.

EXAMPLES

Comparative Example with Iodobenzene Diacetate

Preparation of (1-{6-[trifluoromethyl]pyridin-3-yl}ethyl)(methyl)-λ$^4$-sulfanylidenecyanamide

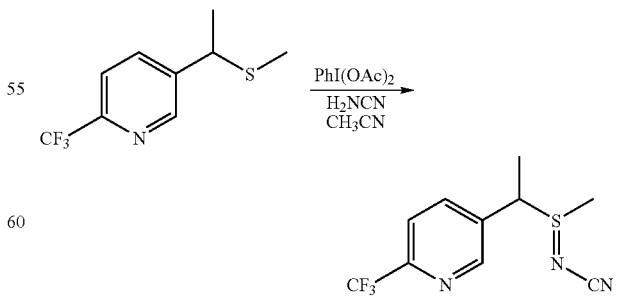

A mixture of 221 g (1.0 mol) of 3-[1-(methylthio)ethyl]-6-(trifluoromethyl)pyridine and 42 g (1.0 mol) of cyanamide in 1200 mL of acetonitrile was cooled below 10° C. To this solution was added 322 g (1.0 mol) of iodobenzene diacetate all at once. The reaction mixture was allowed to stir below 10° C. for 10 min and then the ice-bath was removed. The reaction mixture slowly warmed to room temperature over 1.5 hr, and then slowly exothermed from 22°-30° C. over the next 0.5 hr. The reaction mixture was allowed to return to room temperature, and 800 mL of water was added. Excess oxidant was destroyed by adding ~20 mL of an aqueous solution of sodium meta-bisulfite. To the mixture was added 800 mL of hexanes, the mixture stirred 5 min, and separated. The bottom aqueous layer was returned to the flask, 400 mL of water was added followed by 400 mL of hexanes. The mixture was stirred 5 min and separated. The aqueous layer was again returned to the round-bottom flask and extracted a third time with 400 mL of hexanes. The aqueous layer was concentrated in vacuo until a cloudy two-phase mixture was obtained. This mixture was extracted two times (700 mL, 300 mL) with dichloromethane, the organics combined and dried overnight over MgSO$_4$. After filtration, LC analysis indicated the dichloromethane solution (1560 g) contained a 28:64 (area) ratio of two sulfilimine isomers.

Isomer A:

A portion of sulfilimine solution from above (40 mL) was concentrated in vacuo and exposed to high vacuum to give a thick, orange/amber oil. This oil was dissolved in 10 mL of EtOAc, and 10 mL of hexanes was added. To the cloudy mixture was added 1 mL of EtOAc to give back a clear solution. The flask was scratched with a glass rod to induce crystallization. The mixture was cooled in a refrigerator for 1 hr, filtered and exposed to high vacuum drying to give 1.2 g of a white powder, mp 115°-117° C., >99% (area) LC of the first eluting isomer; $^1$H nmr (CDCl$_3$): δ 8.72 (d, J=2 Hz, 1H), 8.04 (dd, J=2 Hz, 8 Hz, 1H), 7.81 (d, J=8 Hz, 1H), 4.41 (q, J=7 Hz, 1H), 2.62 (s, 3H), 1.90 (d, J=7 Hz, 3H).

Isomer B:

The filtrate from above was concentrated in vacuo to give a thick amber oil (15:67 area ratio of two isomers by LC). This oil was flash chromatographed on silica, eluting with 5% EtOH in CHCl$_3$. Some minor colored material was discarded first. The major sulfilimine isomer (second eluting isomer by LC) was collected next, concentrated in vacuo and exposed to high vacuum drying to give 3.2 g of a thick amber oil. This oil was slurried and scratched with 20 mL of Et$_2$O, cooled in a refrigerator, filtered and exposed to high vacuum drying to give 2.48 g of a white powder, mp 78°-80° C., >99% (area) LC of the second eluting isomer; $^1$H nmr (CDCl$_3$): δ 8.74 (d, J=2 Hz, 1H), 7.95 (dd, J=2 Hz, 8 Hz, 1H), 7.81 (d, J=8 Hz, 1H), 4.45 (q, J=7 Hz, 1H), 2.65 (s, 3H), 1.92 (d, J=7 Hz, 3H).

Example 1

Preparation of (1-{6-[trifluoromethyl]pyridin-3-yl}ethyl)(methyl)-λ$^4$-sulfanylidenecyanamide

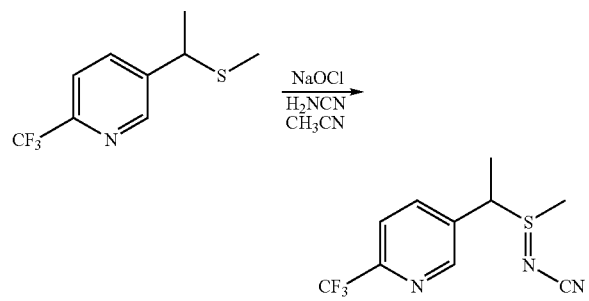

A solution of 22.1 g (0.1 mol) of 3-[1-(methylthio)ethyl]-6-(trifluoromethyl)pyridine and 5.04 g (0.12 mol) of cyanamide in 150 mL of acetonitrile was cooled to −5° C. To this solution was added 150 g (0.115 mol, Clorox™ 5.7% wt) of aqueous NaOCl dropwise over 15 min. The reaction mixture was allowed to stir at −5° C. for 45 min, and then allowed to warm to 5° C. To the mixture was added 5 mL of 25% aq sodium metabisulfite and the two phase mixture was allowed to settle. To the organic phase was added 5.7 mL (0.1 mol) of glacial acetic acid, and the solution concentrated in vacuo to an oil. This oil was dissolved in 70 mL of CH$_2$Cl$_2$ and washed with 50 mL of water. The aqueous layer was reextracted with 30 mL of CH$_2$Cl$_2$. The organics were combined and dried over MgSO$_4$. After filtration, the dichloromethane solution was analyzed by LC and contained 42:52 (area) ratio of isomers A and B above.

Example 2

Preparation of (1-{6-[trifluoromethyl]pyridin-3-yl}ethyl)(methyl)-λ$^4$-sulfanylidenecyanamide

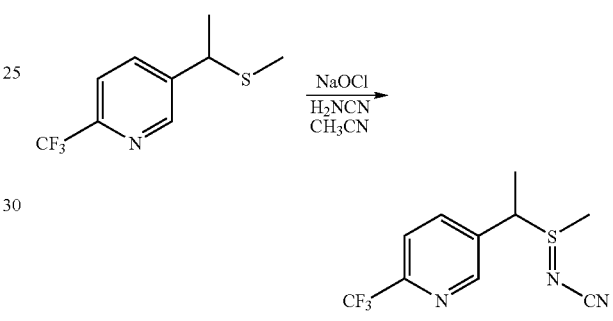

A solution of 110.6 g (0.475 mol, 95% assay) of 3-[1-(methylthio)ethyl]-6-(trifluoromethyl)pyridine and 25.2 g (0.6 mol) of cyanamide in 600 mL of acetonitrile was cooled to −5° C. To this solution was added 750 g (0.575 mol, Clorox™ 5.7% wt) of aqueous NaOCl dropwise over 45 min with the temperature kept below 0° C. The reaction mixture was allowed to stir at −1° C. for 30 min. To the mixture was added 9.5 g (0.05 mol) of sodium metabisulfite in 25 mL of water and the two phase mixture was allowed to settle. The aqueous phase was reextracted 2×'s with 50 mL of acetonitrile. The organics were combined and this acetonitrile/sulfilimine solution was used directly in the following oxidation. LC analysis indicated a 40:54 (area) ratio of two isomers.

Example 3

Preparation of [1-(6-trifluoromethylpyridin-3-yl)ethyl](methyl)-oxido-λ$^4$-sulfanylidenecyanamide

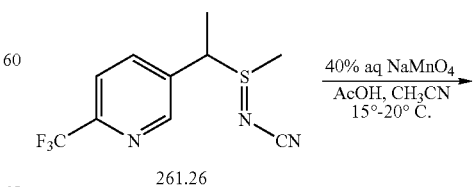

261.26

-continued

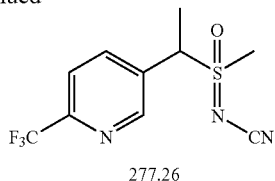
277.26

A mixture of 100 mL of acetonitrile, 200 mL of water, and 160 g (0.45 mol) of a 40% aq solution of NaMnO$_4$ (Aldrich) was cooled to 15° C. To a solution of sulfilimine (~0.475 mol from Example 2) in ~700 mL of acetonitrile was added 26 mL (0.45 mol) of glacial acetic acid. This sulfilimine solution was added over 50 min with rapid stirring to the permanganate mixture. During this time the ice-bath was lowered or raised to maintain a reaction temperature near 19° C. The reaction was allowed to post-react for 45 min. The mixture was cooled to 12° C., and a solution of 171 g (0.9 mol) of sodium metabisulfite in 300 mL of water was added with rapid stirring over 15 min. The mixture was stirred at room temperature for 30 min, and then filtered. The off-white solid was rinsed with 50 mL of acetonitrile. The two phase mixture was transferred to a 2 L separatory funnel, and the aqueous layer discarded. The organic layer was concentrated in vacuo to ~50% wt product This mixture was poured onto 300 mL of rapidly stirred water in an ice-bath. The mixture was stirred cold for 1 h and filtered to give 147.6 g of a white solid. The product was air-dried in a hood to give 116.5 g of product, and further dried in a vacuum oven at 35° C. to give 116.5 g (88% wt) of a white powder. LC analysis indicated a 43:52 (area) ratio of two isomers and a 95% area purity.

Example 4

Preparation of N-Cyano-S-[1-(6-trifluoromethyl-3-pyridinyl)ethyl]-S-methylsulfilimine

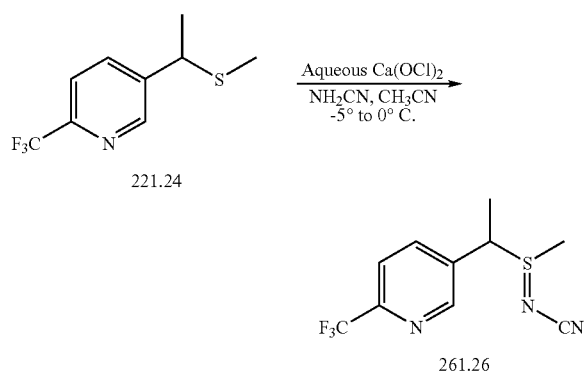

Acetonitrile (50 mL), cyanamide (1.14 grams, 27.1 mmoles) and 3-[1-(methylthio)ethyl]-6-(trifluoromethyl)pyridine (5.00 grams, 22.6 mmoles, 99+% assay) were combined in a 100 mL, 3-necked round bottom flask equipped with a thermowell/K-thermocouple, stopper, nitrogen oil bubbler and magnetic stir bar. The stirred solution was cooled to about −5° C. with an acetone/ice bath. To this solution was added 55.96 grams of an aqueous 6.0 wt % calcium hypochlorite solution (3.36 grams of calcium hypochlorite, 23.5 mmoles, 65% available chlorine) dropwise over 44 minutes. Some undissolved solids were present in the calcium hypochlorite solution and were added as well. The temperature was kept below 0° C. during the addition. The pale yellow reaction mixture was allowed to stir at about 0° C. for 65 minutes. To the yellow reaction mixture was added 0.53 g (2.8 mmoles) of sodium metabisulfite, in portions as a solid to destroy any remaining oxidant. A white flocculant was present in the reaction mixture. It was removed by vacuum filtration of the entire reaction mixture through a medium sintered glass filter funnel. The filtrate was transferred to a separatory funnel and the phases were allowed to settle. The phases were separated and the aqueous phase re-extracted with acetonitrile (10 mL) and (15 mL). Sodium chloride (10.01 grams) was added to the aqueous phase during the second extraction to facilitate a phase break. The organics were combined and this acetonitrile/sulfilimine solution was used directly in the following oxidation. LC analysis indicated a 1.00:1.08 area ratio of the two sulfilimine isomers and showed sulfilimine at 80 area % and sulfoxide (two isomers) at 13 area %.

Example 5

Preparation of N-Cyano-S-[1-(6-trifluoromethyl-3-pyridinyl)ethyl]-S-methylsulfoximine

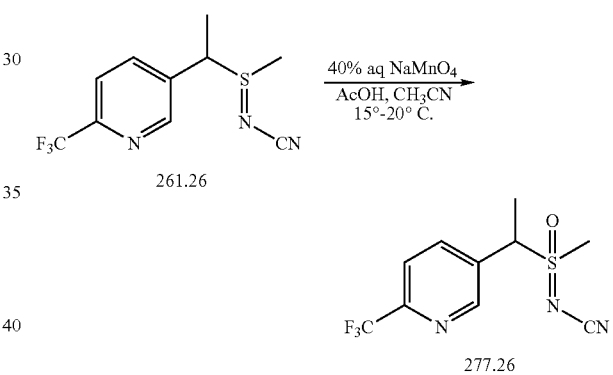

Acetonitrile (5 mL), water (10 mL) and 7.63 grams (21.5 mmoles) of a 40% aqueous solution of NaMnO4 (Aldrich) were combined in a 100 mL three necked, round bottom flask equipped with a magnetic stir bar, pressure equalizing addition funnel, thermowell/K-thermocouple, nitrogen oil bubbler and stopper. A solution of (~22.6 mmoles) sulfilimine in about 70 mL of acetonitrile was filtered through a cone of Whatman filter paper to remove a small amount of white flocculant. To the filtrate was added 1.23 mL (21.5 mmoles) of glacial acetic acid. The resulting solution was loaded to the addition funnel. The sodium permanganate solution was cooled to about 13° C. The sulfilimine solution was added over 60 min with rapid stirring to the permanganate mixture. The temperature ranged from 13 to 18° C. during the addition. The reaction was allowed to post-react for 45 minutes. The dark mixture was cooled to about 12° C., and a solution of 7.75 grams (40.8 mmoles) of sodium metabisulfite in 12 mL of water was added with rapid stirring over 7 minutes. A maximum reaction temperature of about 16° C. occurred during the addition. The reaction mixture was still dark at the end of the addition but gradually lightened to afford an off-white flocculent. A small dark rind remained on the flask sides at this point, but dissipated on continued stirring. The mixture was allowed to warm to room temperature with stirring over 105 minutes. The entire mixture was vacuum filtered through a course sintered glass filter funnel. The tan wet cake was rinsed with acetonitrile (10 mL). The combined filtrate was transferred to a separatory funnel and the phases were allowed to settle. The clear, colorless lower phase (43.0 grams) was removed. The upper organic phase (56.1 grams) was concentrated to a mass of 22.0 grams at a pressure of 70 to 80 mm Hg and a temperature of 20 to 25° C. The resulting two phase mixture was poured into 44.5 grams of well stirred, chilled (<5° C.) water. A white slurry developed and was stirred at <5° C. for about one hour. The solids were collected by vacuum filtration on a course sintered glass filter funnel and the white solid was rinsed with 10 mL of cold water. The product wet cake 5.24 grams was air-dried in a hood overnight to give 4.01 grams (65%) of the desired sulfoximine. LC analysis indicated a 1.04:1.00 (area) ratio of the two isomers and a 94% area purity, with the major impurity being the sulfone (3.5% area).

What is claimed is:

1. A process for preparing sulfilimines of formula (I),

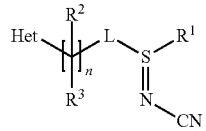
(I)

wherein

Het represents:

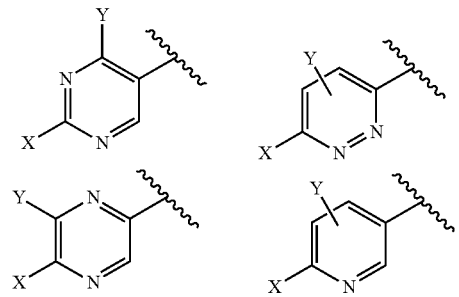

X represents halogen, $C_1$-$C_4$ alkyl, $C_1$-$C_4$ haloalkyl, $C_2$-$C_4$ alkenyl, $C_2$-$C_4$ alkynyl, $C_2$-$C_4$ haloalkenyl, $C_1$-$C_4$ alkoxy, $C_1$-$C_4$ haloalkoxy, CN, $NO_2$, $COOR^4$ or $CONR^4R^5$;

Y represents hydrogen, halogen, $C_1$-$C_4$ alkyl, $C_1$-$C_4$ haloalkyl, $C_2$-$C_4$ alkenyl, $C_2$-$C_4$ alkynyl, $C_2$-$C_4$ haloalkenyl, $C_1$-$C_4$ alkoxy, $C_1$-$C_4$ haloalkoxy, CN, $NO_2$, $COOR^4$, $CONR^4R^5$, or aryl;

n is an integer from 0-3;

L represents either a single bond or —$CH_2$;

$R^1$ represents $C_1$-$C_4$ alkyl, $C_1$-$C_4$ haloalkyl, $C_3$-$C_6$ alkenyl, $C_3$-$C_6$ alkynyl, $C_3$-$C_6$ haloalkenyl, or arylalkyl;

$R^2$ and $R^3$ independently represent hydrogen, halogen, $C_1$-$C_4$ alkyl, $C_1$-$C_4$ haloalkyl, $C_2$-$C_4$ alkenyl, $C_2$-$C_4$ alkynyl, $C_2$-$C_4$ haloalkenyl, $C_1$-$C_4$ alkoxy, $C_1$-$C_4$ haloalkoxy, CN, $SO_mR^6$ where m is an integer from 0-2, arylalkyl, or, alternatively, $R^2$ and $R^3$ and the common carbon to which they attach form a 3-6 membered ring;

$R^4$ and $R^5$ independently represent hydrogen, $C_1$-$C_4$ alkyl, $C_1$-$C_4$ haloalkyl; $C_3$-$C_6$ alkenyl, $C_3$-$C_6$ alkynyl, $C_3$-$C_6$ haloalkenyl, aryl, or arylalkyl; and $R^6$ represents $C_1$-$C_4$ alkyl, $C_1$-$C_4$ haloalkyl, $C_3$-$C_6$ alkenyl, $C_3$-$C_6$ alkynyl, $C_3$-$C_6$ haloalkenyl, or arylalkyl;

which comprises contacting a sulfide of formula (II)

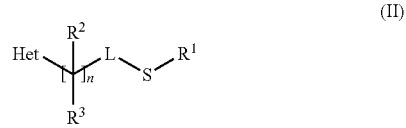
(II)

wherein $R^1$, $R^2$, $R^3$, L, Het and n are as previously defined with cyanamide and hypochlorite solution at a temperature from about −40° C. to about 30° C. in a suitable organic solvent that is essentially inert to the reaction conditions.

2. The process of claim 1 in which Het is (6-substituted) pyridin-3-yl and where X is halogen or $C_1$-$C_2$ haloalkyl and Y is hydrogen.

3. The process of claim 1 in which the sulfilimine has the structure

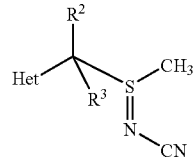

wherein

Het, $R^2$ and $R^3$ are as previously defined, $R^1$ is methyl, n is 1, and L is a single bond.

4. The process of claim 1 in which the temperature is from about −10° C. to about 10° C.

5. The process of claim 1 in which the hypochlorite solution is commercial Clorox bleach which contains about 5 to about 6 weight percent sodium hypochlorite in water.

6. The process of claim 1 in which the organic solvent is a halogenated aliphatic hydrocarbon or an aliphatic nitrile.

7. The process of claim 1 in which the process is conducted in a biphasic solvent system comprising a mixture a halogenated aliphatic hydrocarbon and water.

* * * * *